United States Patent [19]

Jarcho

[11] 4,207,306

[45] Jun. 10, 1980

[54] PROCESS FOR PRODUCING POLYCRYSTALLINE CERAMIC OXIDES

[75] Inventor: Michael Jarcho, Schodack, N.Y.

[73] Assignee: Sterling Drug Inc., New York, N.Y.

[21] Appl. No.: 862,784

[22] Filed: Dec. 21, 1977

Related U.S. Application Data

[60] Division of Ser. No. 764,266, Jan. 31, 1977, Pat. No. 4,097,935, which is a continuation-in-part of Ser. No. 707,315, Jul. 21, 1976, abandoned, which is a continuation-in-part of Ser. No. 593,303, Jul. 7, 1975, abandoned, which is a continuation-in-part of Ser. No. 494,240, Aug. 2, 1974, abandoned.

[51] Int. Cl.$^2$ ............................................. C01G 49/06
[52] U.S. Cl. ................................... 423/633; 106/39.5; 423/625; 423/594; 423/598; 423/636
[58] Field of Search ................ 423/633, 634; 106/39.5

[56] References Cited

U.S. PATENT DOCUMENTS

| | | | |
|---|---|---|---|
| 3,469,942 | 9/1969 | Henneberger et al. | 423/633 |
| 3,987,156 | 10/1976 | Nobuoka | 423/633 |
| 4,006,090 | 2/1977 | Beck | 423/633 |

*Primary Examiner*—Herbert T. Carter
*Attorney, Agent, or Firm*—Paul E. Dupont; B. Woodrow Wyatt

[57] ABSTRACT

A novel ceramic form of hydroxylapatite and a novel ceramic product comprising a mixture of the latter and whitlockite, the preparation of these ceramics and dental restorative compositions and dental and surgical prosthetic materials containing the same are disclosed. Also described is a novel and improved process for producing polycrystalline ceramic oxides.

2 Claims, No Drawings

PROCESS FOR PRODUCING POLYCRYSTALLINE CERAMIC OXIDES

CROSS-REFERENCE TO RELATED APPLICATIONS

This application is a division of copending application Ser. No. 764,266, filed Jan. 31, 1977, now U.S. Pat. No. 4,097,935, issued July 4, 1978 which is a continuation-in-part of application Ser. No. 707,315, filed July 21, 1976 now abandoned which is a continuation-in-part of application Ser. No. 593,303, filed July 7, 1975, now abandoned and which is in turn a continuation-in-part of application Ser. No. 494,240, filed Aug. 2, 1974, now abandoned.

BACKGROUND OF THE INVENTION

1. Field of the Invention

The subject matter of this invention resides in the field of ceramics and finds particular utility in the areas of dentistry, orthopedics, electronics and electrical engineering.

2. Description of the Prior Art

Much current dental research is focused on the preparation of materials which can be used as a substitute for tooth and bone, as a dental restorative material for fillings, caps and crowns and as a prosthetic filling material for bone. Dental research also is directed to preventing the formation of dental plaque, the putative agent of both dental caries and periodontal disease.

Currently used filler materials for dental restorative compositions such as quartz, alumina, silicates, glass beads, etc., bear little chemical or physical resemblance to tooth enamel. A particular deficiency of these materials lies in the incompatibility of the linear coefficients of expansion of filler material and tooth which can eventually result in marginal leakage and new caries formation. The dental profession, therefore, has long desired a dental filling composition with physical properties which closely conform to those of natural tooth structure.

Furthermore, in the field of surgical prosthetic materials, which is currently dominated by high-strength, non-corrosive alloys, there is a recognized need for a material which more closely resembles biological hard tissue as the problems of tissue acceptance and adherence have not as yet been completely resolved [Hulbert, et al., Materials Science Research 5, 417 (1971)].

In research directed to the discovery of effective anti-plaque chemotherapeutic agents there is need for a standard test material having a tooth-like surface with respect to both plaque formation and substantiveness of chemical agents. Although natural teeth have been used for this purpose, these have the drawbacks of being highly variable, relatively unavailable in large numbers, and require elaborate cleaning before use. Consequently there are used other materials upon which dental plaque will accumulate such as powdered hydroxylapatite, acrylic teeth, glass and wire. Although perhaps adequate for studying plaque formation as such, these materials bear little resemblance to the natural tooth surface and are therefore not completely suitable for use in finding effective anti-plaque agents. For example, it is known that chemicals which inhibit plaque formation on teeth do not necessarily do so on glass and wire [Turesky et al., J. Periodontology 43, 263 (1972)]. There is a need then for an inexpensive, readily available material which is chemically similar to tooth enamel, hard, dense, and highly polished.

Hydroxylapatite, $Ca_{10}(PO_4)_6(OH)_2$, also known as basic calcium orthophosphate, occurs as a mineral in phosphate rock. It constitutes the mineral phase of tooth and bone and has been suggested as suited to the various purposes outlined above.

U.S. Pat. No. 2,508,816, issued May 23, 1950 discloses a method for obtaining the hydroxylapatite of tooth enamel and its use in admixture with a synthetic resin as a prosthetic tooth composition. This procedure is lengthy and laborious and limited to producing finely divided hydroxylapatite. Moreover, the method is of course dependent on the availability of a supply of natural teeth.

The use of porous, non-ceramic hydroxylapatite as a filler material in dental cements and filling compositions has been disclosed, e.g. in U.S. Pat. No. 3,873,327, issued Mar. 25, 1975 on an application filed Feb. 28, 1974 and German Offenlegungsschrift No. 2,415,333, published Oct. 17, 1974.

Kutty [Indian J. Cham. 11, 695 (1973)] has reported the results of a study of the thermal decomposition of hydroxylapatite which indicate in summary that "Hydroxylapatite, $Ca_5(PO_4)_3(OH)$, undergoes a slow decomposition when heated at 1250° C. in a current of dry air, forming a mixture of $Ca_3(PO_4)_2$ and $Ca_4P_2O_9$ as confirmed by IR and X-ray diffraction studies."

The report also described the heating of powdered synthetic hydroxylapatite at 1050° C. and 1150° C. for 20 hours. Excepting the statement that the sample heated at 1150° C. underwent partial decomposition as indicated by infrared and X-ray diffraction data, the report neither described nor characterized the products obtained by heating below 1250° C. nor are said products stated or suggested to have any utility.

Bett, et al, [J. Amer. Chem. Soc. 89, 5535 (1967)] described the preparation of particulate hydroxylapatite with stoichiometry varying from Ca/P=1.67 to 1.57. The materials so-produced contained large intercrystalline pores. It was also reported that upon heating up to 1000° C. the calcium-deficient hydroxylapatites underwent partial transformation to the whitlockite phase.

McGee (U.S. Pat. No. 3,787,900, filed June 9, 1971, issued Jan. 29, 1974) disclosed a bone and tooth prosthetic material comprising a refractory compound and a calcium phosphate compound, e.g. whitlockite.

Several attempts have been made to provide a hard, strong macroform of hydroxylapatite. However, none of the previously known forms of hydroxylapatite has proven fully satisfactory. Thus, Della M. Roy and S. K. Linnehan [Nature, 247, 220 (1974); U.S. Pat. No. 3,929,971, filed Mar. 30, 1973, issued Dec. 30, 1975] described an elaborate hydrothermal exchange process whereby the skeletal calcium carbonate of marine coral was converted to hydroxylapatite. The material so produced necessarily retained the high porosity characteristic of the coral structure and moreover had a relatively low tensile strength of about 270–470 psi, a serious disadvantage in a prosthetic material.

Monroe, et al. [Journal of Dental Research 50, 860 (1971)] reported the preparation of a ceramic material by sintering compressed tablets of synthetic hydroxylapatite. The material so produced was actually a mixture of hydroxylapatite and approximately 30 percent α-whitlockite, which is $Ca_3(PO_4)_2$ or tricalcium phosphate, as an ordered mosaic array of polyhedral crystallites, and appeared too porous to make it suitable for use in a dental material.

Rao and Boehm [Journal of Dental Research 53, 1351 (1974)] disclosed a polycrystalline form of hydroxylapatite prepared by isostatically pressing powdered hydroxyapatite in a mold and isothermally sintering the molded form. The resulting ceramic was porous and had a maximum compression strength of approximately 17,000 psi.

Bhaskar et al. [Oral Surgery 32, 336 (1971)] described the use of a biodegradable calcium phosphate ceramic material to fill bone defects. The material is highly porous, is resorbed from the implant site and lacks the strength of a metal or nondegradable ceramic implant.

W. Hubbard (Ph.D. Thesis, Marquette University, 1974) disclosed the sintering of compressed tablets of commercially available tribasic calcium phosphate to produce ceramic materials comprising hydroxylapatite and mixtures of the latter with whitlockite. These materials however were of relatively low density and never exceeded about 40,000 psi in compression strength.

In the field of ceramics in general much effort has been and continues to be expended in an effort to efficiently and economically produce high density ceramics. The techniques most commonly employed generally involve preparation of inorganic powders which are compacted under pressure and then sintered. Powder preparation frequently requires grinding, milling and sieving; and often the sintering must be carried out under pressure. These multistep procedures which also require high pressures are both time-consuming and expensive. Accordingly continuing effort is being made to improve and simplify the methods of ceramics fabrication as indicated by the following references which appear to constitute the most pertinent prior art.

Kamigaito et al. (U.S. Pat. No. 3,903,230, issued Sept. 2, 1975) disclosed a method for producing silicon nitride base ceramics by heating mixed powders of silicon nitride, aluminum, and aluminum nitride under a high pressure or no pressure. However, the specification states that the density of the sintered material was increased if the sintering was carried out under pressure and the single example of sintering in the absence of applied pressure resulted in a somewhat porous ceramic.

Wainer et al. (U.S. Pat. No. 3,096,144, issued July 2, 1963) disclosed a method of making inorganic oxide filaments by drying a thin film of a colloidal dispersion of an inorganic oxide to produce porous fibers of the latter which were then sintered to produce dense fibers. The process is of course limited to the production of inorganic filaments.

Cox (U.S. Pat. No. 3,278,263, issued Oct. 11, 1966) and Robbins (U.S. Pat. No. 3,778,373, issued Dec. 11, 1973) disclosed ferromagnetic chromium dioxide and iron-containing ferromagnetic chromium oxide each of which were prepared by essentially the same process which involved precipitation of the chromium oxides from aqueous solution followed by heating or calcining at 200° C.–1000° C. Production of the ultimate product, however, required oxidation at elevated pressure and temperature.

Grimes et al. (U.S. Pat. No. 3,826,755, issued July 30, 1974) disclosed a process for precipitating gels of various metal oxides by complexing a metal ion with a water-soluble organic polymer followed by reaction with hydroxide ion. The gels could then be dried and fired. It appears that the presence of the organic polymers in the gels would preclude formation of substantially non-porous ceramics on firing.

Miller (U.S. Pat. No. 3,066,233, issued Nov. 27, 1962) disclosed ferrite transducers which were produced by mixing milled ferrite powder with binders, gelling agents and wetting agents to give a thick gel which was then aerated, poured into a mold and fired. The product had a cellulated, sponge-like construction.

3. Patent Activities of Others

Terwilliger et al. (U.S. Pat. No. 3,992,497, issued Nov. 16, 1976) disclosed a method of sintering silicon nitride powders in the absence of pressure to effect densification thereof. However this method required that the silicon nitride and a sintering aid (MgO) be subjected to a complex wet-milling process, dried and dry-pressed in a mold at 50,000 psi prior to sintering.

SUMMARY OF THE INVENTION

It is a primary purpose of this invention to provide as a new article of manufacture a novel ceramic form of hydroxylapatite which is useful as a filler in dental cements and restorative compositions, as a dental and surgical prosthetic material, and in the evaluation of dental plaque inhibiting agents, and which is free of the various disadvantages inherent in the materials known in the art.

As more particularly characterized hereinbelow, the new ceramic form of hydroxylapatite afforded by this invention is comprised of substantially pure hydroxylapatite which is hard, dense, and non-porous and which takes a high polish. Chemically but not physically it is similar to tooth enamel. Moreover, this new material can be prepared in a relatively simple manner from inexpensive starting materials and is obtained in uniform quality.

The incorporation of the novel ceramic form of hydroxylapatite in dental restorative compositions provides a dense filler material which has a coefficient of expansion virtually identical to that of natural tooth enamel.

The dental and surgical implant material made available by the instant invention is hard, strong, and completely bio-compatible, and can be fabricated in any desired shape without the need for high pressure or other elaborate techniques. Moreover, as described in detail hereinbelow, when desired, porosity can be imparted to such material in a controlled manner.

As will be apparent, the characteristics of the new article of manufacture herein described and claimed make it ideally suited to the fabrication of discs, plates, rods, etc. for use in testing dental anti-plaque agents.

It is another purpose of this invention to provide as a new article of manufacture a novel biphasic ceramic material comprising hydroxylapatite and whitlockite. As described more completely hereinbelow this biphasic ceramic is hard, dense, non-porous, bio-compatible, easily fabricated in any desired shape or form, and is therefore useful as a strong dental and surgical implant material.

This invention also provides a novel and improved process for producing ceramic oxides such as magnesia, ferric oxide, alumina, barium titanate and the ferrites. The process advantageously avoids the usual and often complex steps of powder preparation, pressing and firing and is accordingly more efficient and economical. Moreover, the properties of the ceramics produced by the present process are generally superior or at least equivalent to those of the ceramics now being produced commercially.

DETAILED DESCRIPTION OF THE INVENTION

The invention sought to be patented resides, in an article of manufacture aspect, in a novel physical form of hydroxylapatite which is distinguished from the biological and geological forms and from all previously known synthetic forms as hereinafter indicated. This novel form comprises substantially pure hydroxylapatite in the form of a strong, hard, dense, white, translucent, isotropic, polycrystalline sintered ceramic material having an average crystallite size in the approximate range 0.2 to 3 microns, a density greater than 98 percent of the theoretical density of hydroxylapatite, and being further characterized by the absence of pores and by cleavage along smooth curved planes. Moreover, as ordinarily produced, the above described material is non-birefringent under polarized light; has a linear thermal coefficient of expansion in the approximate range 10 to 12 ppm per degree centigrade, a Knoop hardness in the approximate range 470 to 500, a modulus of elasticity of approximately $5-6 \times 10^6$ psi, a compression strength in the approximate range 90,000 to 150,000 psi, and a tensile strength in the approximate range 10,000 to 30,000 psi. In view of the known dependence of compression and tensile strengths on the shape, dimensions and surface characteristics of the material tested it will be appreciated that the ceramic hydroxylapatite provided by this invention, when suitably fabricated, can have compression and tensile strengths substantially greater than 150,000 and 30,000 psi respectively.

The term dense as used herein designates a highly compact arrangement of particles substantially lacking spaces or unfilled intervals therebetween.

In contrast to the above-described form of hydroxylapatite, geological hydroxylapatite and synthetic hydroxylapatite prepared by hydrothermal processes are macrocrystalline, fracture along flat planes, and are birefringent. Biological hydroxylapatite is distinguished by generally containing significant amounts of carbonate ion in the apatite lattice and in its purest state, i.e., in tooth enamel, by being anisotropically arranged in coiled radiating rods, so that it fractures in straight lines along the interface of these enamel rods and has a comparatively low tensile strength of 1500 psi.

The ceramic hydroxylapatite of the present invention can be fabricated into any desired form or shape employing conventional modes of fabrication such as molding, casting, machining and the like. In such manner the ceramic can be produced as, for example, a flat sheet of any desired thickness, a cylinder, a cone, a sphere etc.

In addition to the above-described properties of the novel ceramic form of hydroxylapatite provided by this invention this material is also completely bio-compatible and therefore eminently suitable as a dental and surgical prosthetic material. Thus, this ceramic can be cast or machined into dental crowns, artificial teeth, bone and joint prostheses, cannulae, anchoring devices for artificial limbs which can be attached to bone and protrude through the skin, and test surfaces for the study of dental plaque, caries formation, arthritis and other diseases which may affect teeth and bone. Suitably milled, the novel hydroxylapatite ceramic of this invention can be used as synthetic canncellus bone to repair bone defects, as an abrasive, and composited with standard resins as a dental restorative composition as described hereinbelow.

As a test surface for the evaluation of dental plaque-inhibiting agents the hydroxylapatite ceramic of this invention can be fabricated into bodies of any suitable size and shape, preferably of a size and shape which can be easily inserted into a standard test tube. This is conveniently accomplished by cutting or machining large plate-like pieces of dried filter cake to an appropriate size and then sintering. The sintered products are highly polished using standard lapidary techniques and the resulting bodies are then used as substrates in evaluating dental plaque-inhibiting agents according to the procedures described by Turesky, et al., supra. After use the ceramic bodies are simply re-polished to provide a new test surface.

As ordinarily produced the hydroxylapatite ceramic of this invention is dense and non-porous, and whereas a non-porous material is essential for dental applications, a certain degree of porosity in implant devices may be advantageous in permitting circulation of body fluids and tissue ingrowth. Varying degrees of porosity can be imparted to the instant hydroxylapatite ceramic in a manner similar to that described by Monroe, et al., supra. Thus, organic materials such as starch, cellulose, cotton, or collagen in amounts ranging from about 5 to 25 percent by weight are admixed with the gelatinous precipitate of hydroxylapatite. During the subsequent sintering process the organic materials are burned out thereby creating holes and channels in the otherwise non-porous ceramic product. Alternatively, porosity can be produced mechanically by drilling or machining holes and openings in the non-porous ceramic.

In such manner an artifical tooth composed of the hyudroxylapatite ceramic of this invention can be made porous at the point of implantation while the exposed tooth surface remains non-porous. Implantation can be accomplished as reported by Hodosh, et al., Journal of the American Dental Association 70, 362 (1965). Alternatively the instant hydroxylapatite ceramic can be composited with a polymerizable of polymerized bonding material as described herein below and the resulting composition used as a coating for metal implants as described in U.S. Pat. No. 3,609,867, issued Oct. 5, 1971.

As described more fully hereinbelow it is also possible too impart to the instant hydroxylapatite ceramic an alkaline surface. Thus by adding a small excess of calcium ion to the aqueous suspension of hydroxylapatite the ceramic ultimately produced retains all of the desirable characteristics described above and in addition has a surface pH of about 10-12. An implant device fabricated from such material can be of advantage in reducing the generally acidic state of physiologically traumatized area, e.g. a dental or surgical implant site and thereby reduce inflammation and promote more rapid healing.

In a second article-of-manufacture aspect the invention sought to be patented resides in a strong, hard, dense, white, isotropic, polycrystalline sintered ceramic material comprising as one phase from about 20 to 95% by weight of hydroxylapatite and as a second phase from about 5 to 80% by weight of whitlockite and being characterized by the absence of pores and by cleavage along smooth curved planes.

Whitlockite, also known as tricalcium phosphate, is a mineral having the chemical formula $Ca_3(PO_4)_2$ and which may exist in either an $\alpha$ or $\beta$ crystalline phase.

The term whitlockite as used herein designates either the α or the β phase or a mixture of the two phases.

The biphasic ceramic of this invention remains a non-porous polycrystalline material irrespective of the relative concentrations of hydroxylapatite and whitlockite contained therein. However it will be appreciated that hydroxylapatite and whitlockite have different physical properties, and therefore the physical properties, e.g. density and optical properties of the biphasic ceramic will depend on the relative amounts of hydroxylapatite and whitlockite present therein. For example the theoretical density of whitlockite is less than that of hydroxylapatite and accordingly the observed density of a sample of biphasic ceramic containing about 40% hydroxylapatite and 60% whitlockite was 2.98 g/cm$^3$ compared to a density of 3.10 g/cm$^3$ for a sample of hydroxylapatite ceramic.

The above-described biphasic ceramic is also biocompatible and therefore suitable as a dental and surgical prosthetic material. Thus, this material can be cast or machined into bone and joint protheses or into any shape suitable for filling a void or defect in a bone. The biphasic ceramic is also suitable as a test surface for the study of dental plaque, caries formation, arthritis and other diseases which may affect teeth and bone. In finely divided form this material can be used as synthetic cancellus bone and it can be composited with standard resins as a dental restorative composition.

As ordinarily produced the biphasic ceramic of this invention is non-porous. However, if desired, varying degrees of porosity can be imparted to the ceramic as described hereinabove for the novel ceramic form of hydroxylapatite.

The biphasic ceramic may also be rendered acid resistant by fluoridation as described hereinbelow for ceramic hydroxylapatite.

In a process aspect the invention provides a process for preparing a substantially non-porous, polycrystalline, sintered ceramic which comprises reacting calcium ion with phosphate ion in aqueous medium at a pH of about 10-12 to produce a gelatinous precipitate of a phosphate of calcium having a molar ratio of calcium to phosphorus between the approximate molar ratio of calcium to phosphorus in whitlockite, i.e. 1.50 and that in hydroxylapatite, i.e. 1.67, separating said precipitate from solution, heating said precipitate up to a temperature of at least approximately 1000° C. but below that at which appreciable decomposition of hydroxylapatite occurs, and maintaining said temperature for sufficient time to effect the sintering and substantially maximum densification of the resulting product.

More particularly the invention sought to be patented resides in the method of preparation of the above-described novel ceramic form of hydroxylapatite which comprises the steps of precipitating from aqueous medium at a pH of about 10-12 hydroxylapatite having a molar ratio of calcium to phosphorus of about 1.67, separating the precipitated hydroxylapatite from the solution, and heating the hydroxylapatite thus obtained at a temperature and for a time sufficient to effect the sintering and substantially maximum densification of said hydroxylapatite with essentially no decomposition thereof.

Thus, hydroxylapatite is precipitated from aqueous medium by reacting calcium ion with phosphate ion at a pH of about 10-12. Any calcium- or phosphate-containing compounds which provide calcium and phosphate ions in aqueous medium are suitable provided that the respective counter ions of said compounds are easily separated from the hydroxylapatite product, are not themselves incorporated in the hydroxylapatite lattice, or otherwise interfere with precipitation or isolation of substantially pure hydroxylapatite. Compounds which provide calcium ion are, for example calcium nitrate, calcium hydroxide, calcium carbonate and the like. Phosphate ion may be provided by diammonium hydrogen phosphate, ammonium phosphate, phosphoric acid and the like. In the present method calcium nitrate and diammonium hydrogen phosphate are the preferred sources of calcium and phosphate ions respectively.

The preparation of the instantly claimed novel form of hydroxylapatite is conveniently carried out as follows: First, calcium nitrate and diammonium hydrogen phosphate in a molar ratio of 1.67 to 1 are interacted in aqueous solution at a pH of about 10-12 to produce a gelatinous precipitate of hydroxylapatite. The procedure described by Hayek, et al., Inorganic Synthesis 7, 63 (1963) is satisfactory for this purpose. The gelatinous suspension of hydroxylapatite thus obtained is then allowed to remain in contact with the original solution for a time sufficient to allow the calcium to phosphorus ratio of the suspended hydroxylapatite to reach a value of about 1.67. This is conveniently accomplished either by stirring the suspension at room temperature for a period of not less than 24 hours, or by boiling the suspension for a period of 10 to 90 minutes, or by a combination of boiling followed by a standing at room temperature. Preferably the suspension is boiled for 10 minutes and then allowed to stand at room temperature for 15-20 hours. The hydroxylapatite is then separated from the solution by suitable means, for example by centrifugation and vacuum filtration. The gelatinous product thus collected contains a large amount of occluded water, much of which can be removed by pressing. If desired, the resulting wet clay-like material can be cut or shaped into a convenient form, or, alternatively, cast in a suitable mold. It should be noted that ordinarily a shrinkage of approximately 25 percent occurs when the wet hydroxylapatite is dried and a further shrinkage of about 25 percent takes place during the sintering hereinafter described. This should of course be taken into account when shaping or molding the material. The wet product may be slowly heated up to the sintering temperature of 1000° C. to 1250° C. at which point all remaining water will have been driven off. Maintaining the temperature at 1000° C. to 1250° C. for approximately 20 minutes to 3 hours will then effect the sintering and substantially maximum densification of the product. Ordinarily it is convenient to isolate the dried product prior to sintering. Thus the wet product may be dried at about 90° C. to 900° C. for approximately 3 to 24 hours or until the water content thereof has been reduced to 0 to about 2 percent. It is generally preferred to use drying conditions of approximately 90° C. to 95° C. for about 15 hours or until the water content has been reduced to about 1 to 2 percent. The hydroxylapatite obtained in this manner is brittle and porous, but has considerable mechanical strength. Some separation or cracking of the clay-like material may occur on drying especially if a thick filter cake is used. However, pieces as large as 100 cm$^2$ and 3 mm. in thickness are readily obtained. Separation or cracking during drying can be minimized or prevented by adding to the suspension of freshly precipitated hydroxylapatite about 0.4 to 0.6 percent of an organic binder such as collagen, powdered cellulose or cotton, about 0.5 percent of collagen being preferred. The organic binder is volatilized during subsequent sintering and the physical characteristics of the ceramic product appear substantially unchanged from those of the product produced in the absence of such a binder. Of course, the use of substantially larger amounts of organic binder will result in a porous ceramic product as described hereinafter. Other conventional organic and inorganic binders known in the ceramics art can also be used.

It is usually convenient at this stage to further cut or shape the dried hydroxylapatite into roughly the form desired as the end product, taking into account the shrinkage mentioned above which occurs on sintering.

The bodies of hydroxylapatite prior to sintering should be uniform and free of defects. The presence of cracks or fissures can cause the pieces to fracture during the sintering process. The products are then sintered at about 1000° C. to 1250° C. for approximately 20 minutes to three hours, the temperatures and times being inversely related. Sintering is preferably effected at 1100° C. to 1200° C. for approximately 0.5 to 1 hour. The hard, dense ceramic articles so-produced can then be polished or machined using conventional techniques.

It is critical, in the above process, to prepare the hydroxylapatite as a gelatinous precipitate from aqueous solution for it is only in this cohesive gelatinous state that hydroxylapatite can be shaped or molded and then dried and sintered to produce a ceramic body. Dry particulate or granular hydroxylapatite cannot be reconstituted into this cohesive gelatinous state. If, for example, powdered hydroxylapatite is suspended in water and filtered there is obtained a non-cohesive, particulate filter cake which simply dries and crumbles and cannot be shaped, molded or converted into a ceramic body. Moreover, although powdered hydroxylapatite can be mechanically compressed into a shaped body, such as a tablet, when sintered according to the method of this invention the product obtained is highly porous and does not fracture along smooth planes but simply shatters into rough pieces.

Although the formation of hydroxylapatite in aqueous medium is a complex and incompletely understood process, it is generally believed that calcium and phosphate ions initially combine to form a calcium-deficient hydroxylapatite having a calcium-to-phosphorus ratio of about 1.5. In the presence of calcium ion, this species then undergoes slow transformation to hydroxylapatite with a calcium-to-phosphorus ratio of 1.67. [Eanes et al., Nature 208, 365 (1965) and Bett et al., J. Amer. Chem. Soc. 89, 5535 (1967)]. Thus, in order to obtain a ceramic comprising substantially pure hydroxylapatite it is imperative in the process of this invention that the initial gelatinous precipitate of hydroxylapatite be allowed to remain in contact with the original solution for a time sufficient to allow the calcium to phosphorus ratio thereof to reach a value of about 1.67. In practice the calcium to phosphorus ratio was determined within the limits of accuracy of about ±0.05, i.e having an observed value in the approximate range 1.62–1.72. Substantial deviation from this range results in a different ceramic product as described below. For example, if hydroxylapatite is precipitated at room temperature and collected within 2 hours following precipitation the calcium to phosphorus ratio thereof is found to be about 1.55–1.57 and the ceramic ultimately produced therefrom is opaque and found by X-ray diffraction to be a mixture comprising hydroxylapatite and whitlockite. In fact, as described more particularly hereinbelow, material having a calcium to phosphorus ratio substantially less than about 1.67 is useful in the preparation of the biphasic ceramic described hereinabove.

On the other hand, if the calcium to phosphorus ratio of the precipitate is substantially greater than 1.67 the resulting hydroxylapatite ceramic has a surface pH of about 10–12 but otherwise is the same as the product produced when the calcium to phosphorus ratio is 1.67.

In view of the incompletely understood mode of formation of hydroxylapatite in aqueous medium and because of the somewhat limited accuracy of the ordinary analytical methods available to determine calcium and phosphate ion concentrations it is usually advantageous to monitor the hydroxylapatite formation as described hereinbelow in order to ascertain that the desired calcium to phosphorus stoichiometry (i.e. Ca/P=1.67) has been achieved and that the product when sintered will comprise substantially pure hydroxylapatite.

The temperature and duration of sintering are also critical to the process. Thus, unsintered hydroxylapatite having the desired calcium-to-phosphorus ratio of about 1.67 can be converted to the ceramic of this invention by heating at a temperature of from about 1000° C. to 1250° C. At 1000° C. complete sintering and maximum densification may require 2–3 hours while at 1250° C. the process may be complete in 20–30 minutes. It is preferred to effect sintering at a temperature of approximately 1100° C. for about one hour. A temperature substantially below 1000° C. will result in incomplete sintering irrespective of the length of heating whereas heating substantially above 1250° C. for more than one hour will result in partial decomposition of hydroxylapatite to whitlockite and tetracalcium phosphate ($Ca_4P_2O_9$).

In a further process aspect the invention sought to be patented resides in the method of preparation of the above described biphasic ceramic comprising one phase of hydroxylapatite and a second phase of whitlockite which method comprises the steps of precipitating from aqueous solution at a pH of about 10–12 a calcium phosphate compound having a molar ratio of calcium to phosphorus less than about 1.67, but not less than about 1.50, separating the precipitate from the solution and heating the solid thus-obtained at a temperature and for a time sufficient to effect the sintering and substantially maximum densification thereof.

In practice a calcium phosphate compound having an observed calcium to phosphorus ratio in the approximate range 1.44–1.60, preferably about 1.46–1.57 is obtained by interacting calcium ion with phosphate ion in aqueous medium at pH 10–12 employing the same sources of calcium and phosphate ions described hereinabove for the preparation of single phase hydroxylapatite. Calcium nitrate and diammonium hydrogen phosphate are the preferred reagents.

Thus the instantly claimed biphasic ceramic may be prepared by interacting calcium nitrate and diammonium hydrogen phosphate in a molar ratio of about 1.67 to 1, i.e. as described hereinabove for the preparation of single phase ceramic hydroxylapatite provided that the initial gelatinous precipitate is not heated and is allowed to remain in contact with the original solution for a period not to exceed about 4 hours or alternatively that the molar ratio of calcium to phosphorus of the precipitate not be allowed to reach 1.67. In practice the calcium to phosphorus ratio is preferably not allowed to exceed an observed value of about 1.60.

As described hereinabove for the preparation of single phase ceramic hydroxylapatite, the calcium phosphate precipitate is separated from the solution, washed, optionally shaped or molded into a convenient form, and if desired dried and isolated prior to sintering.

The suspension of freshly precipitated calcium phosphate may also be treated with organic binders or fluoride ion as described hereinabove for single phase hydroxylapatite.

Sintering is effected by heating at about 1000° C. to 1350° C. for approximately 20 minutes to 3 hours.

The amount of whitlockite contained in the ceramic so-produced will depend on the time at which the precipitate is separated from the original solution and may range from about 2 to 86%. Thus when the product is isolated 5 minutes following precipitation the calcium to phosphorus ratio thereof is 1.55 and the ceramic ultimately produced therefrom contains about 77% whitlockite. If the product is isolated 2 hours after precipitation the calcium to phosphorus ratio thereof is 1.57 and the resulting ceramic contains about 61% whitlockite. Isolation of the product 4.5 hours following precipitation ultimately affords a ceramic containing an estimated 2% whitlockite, an amount barely detectable by X-ray diffraction which has a minimum concentration sensitivity of 2–3%. Of course, if the product is allowed to remain in contact with the original solution beyond about 7 hours the ceramic ultimately obtained is substantially single phase hydroxylapatite.

It will be appreciated that because of the time dependent nature of the above-described process it is possible, particularly in large scale production, for the calcium to phosphorus ratio to change during the isolation step possibly leading to an inhomogeneous product. Accordingly, it is preferable to prepare the biphasic ceramic by reacting calcium ion with phosphate ion in a molar ratio of less than 1.67 to 1. In this way the molar ratio of calcium to phosphorus can be allowed to reach its equilibrium value which will of necessity be less than 1.67 thereby assuring production of the biphasic ceramic.

In order to ensure the production of biphasic ceramic having the required calcium to phosphorus ratio and hence the desired ultimate composition, the reaction can be monitored, as described hereinbelow, by removing an aliquot of the suspension, separating, drying and sintering the product and subjecting the resulting ceramic to elemental and X-ray analysis. As desired additional calcium or phosphate ion can then be added to the suspension which is allowed to equilibrate prior to isolation and sintering.

Thus the preparation of the instantly claimed biphasic ceramic is conveniently carried out as described hereinabove for the preparation of single phase ceramic hydroxylapatite with the exception that the reactants viz. calcium nitrate and diammonium hydrogen phosphate are interacted in an approximate molar ratio of 1.50–1.66 to 1 to produce ceramics comprising about 20–95% hydroxylapatite and about 5–80% whitlockite.

The ceramic may be further enriched in the whitlockite phase by combining the features of the two preceding procedures, i.e. by interacting calcium ion with phosphate ion in an approximate molar ratio of 1.50–1.66 to 1 and isolating the precipitated calcium phosphate compound within a short time, preferably about 5 minutes to 4 hours, following precipitation. Ceramics so-produced comprise about 10–30% hydroxylapatite and 70–90% whitlockite.

It will of course be understood that since the calcium to phosphorus ratio of whitlockite is 1.50 and that of hydroxylapatite is 1.67 a mixture of the two will have a calcium to phosphorus ratio between 1.50 and 1.67. Accordingly any ceramic produced in accordance with this invention having a calcium to phosphorus ratio of about 1.50 and indicated by X-ray diffraction to be a mixture of whitlockite and hydroxylapatite will of necessity contain lattice defects, i.e. a certain number of calcium ion positions in the crystal lattice will remain unoccupied. Notwithstanding this calcium deficiency these materials nonetheless retain the useful properties described above for the biphasic ceramics.

As noted hereinabove a calcium to phosphorus ratio substantially greater than 1.67 will result in an alkaline hydroxylapatite ceramic. When the latter is the desired product it is convenient to ensure its production by monitoring the reaction by work up of an aliquot as described below and adding additional calcium ion as required. Generally a molar excess of about 2 to 3 percent is sufficient.

Because of the above-described observed relationship between the ceramic products of this invention and their respective calcium to phosphorus ratios it is usually preferred, in order to ensure the production of a given desired ceramic product of this invention described hereinabove, viz. the substantially pure ceramic hydroxylapatite, the biphasic ceramic comprising hydroxylapatite and whitlockite, or the alkaline ceramic hydroxylapatite, to monitor the reaction by removing and processing an aliquot of the suspension and subjecting the resulting ceramic to elemental and X-ray analyses. If these analyses indicate that the required stoichiometry has not been achieved and hence that the desired ultimate product will not be obtained, it is then necessary to ascertain what amount of either calcium ion (if the calcium to phosphorus ratio is too low) or phosphate ion (if the calcium to phosphorus ratio to too high) must be added to the suspension to afford the desired final product. This can be determined by any suitable method, and is conveniently and simply carried out by graded additions of calcium ion or phosphate ion as may be required, to several aliquots of the suspension, and then processing these suspensions to the respective ceramic products which are subjected to elemental and X-ray analyses. After selection of the preferred ceramic from among the samples so-produced, there can of course be calculated the amount of either calcium or phosphate ion to be added to the main suspension. Following addition of the required amount of calcium or phosphate ion the suspension is stirred for approximately 10 to 24 hours and the product is isolated as previously described.

In yet a further process aspect, the invention sought to be patented resides in a process for producing a dense polycrystalline ceramic selected from the group consisting of magnesium oxide, ferric oxide, aluminum oxide and the ferrites having the formula $MFe_2O_4$ where M is a divalent metal selected from the group consisting of nickel, zinc and cobalt which comprises reacting magnesium ion, ferric ion, aluminum ion or a 1:2 molar ratio of a divalent metal ion M(II) and ferric ion with hydroxide ion in aqueous medium to produce a gelatinous precipitate of the corresponding hydroxide, hydrous oxide or mixture of these; separating the gelatinous precipitate from solution; heating the gelatinous precipitate up to a temperature of at least 1000° C. but below that at which decomposition occurs; and maintaining said temperature for sufficient time to effect the sintering and substantially maximum densification of the resulting product.

In one particular embodiment of the above process aspect of the invention there is provided a process for producing a dense polycrystalline magnesium oxide ceramic which comprises reacting magnesium ion with hydroxide ion in aqueous medium to produce a gelatinous precipitate of magnesium hydroxide; separating the gelatinous precipitate from solution; heating the gelatinous precipitate up to a temperature of about 1600° C.; and maintaining said temperature for approximately 6 to 60 hours.

The magnesium oxide ceramic produced is useful as an electrical and thermal insulating material.

Another particular embodiment of the above process resides in a method for producing a dense polycrystalline ferric oxide ceramic which comprises reacting ferric ion with hydroxide ion in aqueous medium to produce a gelatinous precipitate of hydrous ferric oxide; separating said gelatinous precipitate from solution; heating the gelatinous precipitate up to a temperature of about 1100° C.; and maintaining said temperature for approximately one hour.

The ferric oxide ceramic produced is useful as an industrial abrasive.

A further particular embodiment of the above process resides in a method for producing a polycrystalline aluminum oxide ceramic which comprises reacting aluminum ion with hydroxide ion in aqueous medium to produce a gelatinous precipitate of hydrous aluminum oxide; separating the gelatinous precipitate from solution; and heating the gelatinous precipitate at a temperature and for a time sufficient to effect the sintering and substantially maximum densification thereof.

Aluminum oxide ceramic is useful in the manufacture of lamps and various electronic substrates.

In yet another particular embodiment the above process provides a method for producing a dense polycrystalline ferrite ceramic having the formula $MFe_2O_4$ wherein M is a divalent metal selected from the group consisting of nickel, zinc and cobalt, which comprises reacting a 1:2 molar ratio of a divalent metal M(II) and ferric ion with hydroxide ion in aqueous medium to produce a gelatinous precipitate consisting of $M(OH)_2$ and hydrous ferric oxide; separating the gelatinous precipitate from solution; heating the gelatinous precipitate up to a temperature of about 1000° C. to 1300° C. and maintaining said temperature for approximately 1 to 3 hours.

The ferrites are useful in the manufacture of computer memories, microwave devices and permanent magnets.

Thus the preparation of ceramic oxides in accordance with the above process is conveniently carried out by interacting an aqueous solution of an appropriate metal salt, or in the case of the ferrites, a 1:2 mixture of a divalent metal salt and an iron (III) salt with a substantially stoichiometric amount of ammonium or sodium hydroxide. The resultant gelatinous precipitate is separated from the solution by suitable means, for example by centrifugation and decantation; washed with water to remove soluble impurities; and then collected by vacuum filtration. If desired the resulting wet clay-like material can be shaped or molded into a convenient form. The wet product is then heated up to the sintering temperature at which point all remaining water will have been driven off and the product converted to the anhydrous oxide. The latter is then maintained at the appropriate sintering temperature for a time sufficient to effect substantially maximum densification thereof.

Depending on the nature of the metal, reaction with hydroxide ion in aqueous solution precipitates the metal hydroxide or hydrous metal oxide. Thus magnesium, nickel, zinc and cobalt ions precipitate as the hydroxides whereas iron (III) and aluminum ion precipitate as the hydrous oxides. Accordingly a 2:1 mixture of iron (III) and a divalent metal ion such as nickel (II), cobalt (II) or zinc (II) precipitates as a mixture of divalent metal hydroxide and hydrous ferric oxide. Upon heating, these initial precipitates are converted to the anhydrous oxides and ultimately to ceramic oxides as follows:

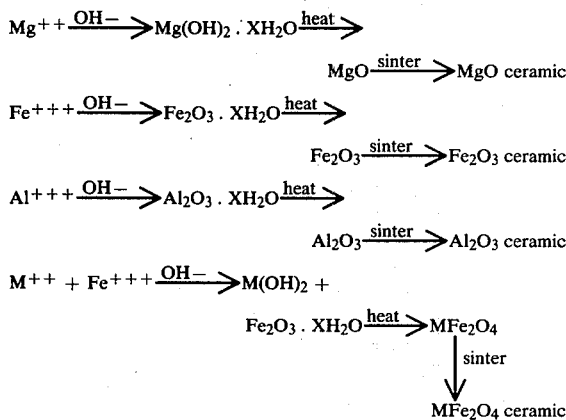

In the above reactions any water-soluble salts of magnesium, iron (III), aluminum, nickel (II), zinc or cobalt (II) can serve as sources of the respective metal ions provided the counter anions of said salts are easily separated from the precipitated products, are not themselves incorporated in the oxide or hydroxide lattices or otherwise interfere with isolation of the product in the desired state of purity. For example, the salts which can be employed include magnesium nitrate, magnesium chloride, magnesium acetate, ferric nitrate, ferric chloride, ferric ammonium sulfate, ferric bromide, nickel nitrate, nickel chloride, nickel acetate, cobalt nitrate, cobalt chloride, cobalt acetate, zinc nitrate, zinc chloride, zinc acetate, aluminum nitrate, aluminum chloride, aluminum acetate and the like.

As sources of hydroxide ion there can be used for example ammonium hydroxide and the alkali metal hydroxides.

It will of course be appreciated that both the nature of the hydroxide ion source and the concentration of hydroxide ion are factors to be considered in the present process. Thus the use of excess ammonium hydroxide should be avoided with metal ions which form stable ammonia complexes e.g. zinc, cobalt and nickel; and stoichiometric amounts of hydroxide ion should of course be used to precipitate metal ions such as aluminum, zinc, and to a lesser extent cobalt which form hydroxides which are soluble in excess alkali.

Ordinarily it is convenient to isolate the partially dried product prior to sintering. Thus the wet product may be dried at about 25° C. to 100° C. for approximately 10 to 60 hours or until substantially all the occluded water has been removed. Considerable separation or cracking may occur on drying. This can be minimized by carefully controlling temperature, humidity and drying time in accordance with techniques known in the ceramics art or alternatively by adding small amounts of organic binders to the freshly precipitated metal oxide as described above for hydroxylapatite.

It is important to control the rate and duration of heating of the partially dried oxides up to the sintering temperature in order to ultimately obtain crack-free sintered ceramic oxides. This is, of course, particularly important in the preparation of large ceramic bodies. The optimum conditions for a particular oxide are easily determined by a technician skilled in the art. Thus, for example partially dried samples of nickel ferrite were introduced into a furnace at 350° C. and held there for one hour. The temperature was increased to 500° C. at a rate of 100° C./hr. and then at a rate of 200° C./hr. up to a final sintering temperature in the approximate range 1000° C. to 1300° C. Sintering produced substantially crack-free sintered nickel ferrite ceramic.

The temperature and duration of sintering depend of course on the refractory properties of a given metal oxide. Thus magnesium oxide was sintered at about 1600° C. for approximately 6 to 60 hours, preferably about 50 hours, whereas ferric oxide was sintered at about 1100° C. for approximately one hour. The ferrites were sintered at a temperature in the approximate range 1000° C. to 1300° C. for about 1 to 3 hours, preferably at about 1200° C. to 1300° C. for about 3 hours.

Although the instant process as above-described depends initially on the formation of a water-insoluble hydroxide or hydrous oxide, it is nevertheless possible to prepare the ceramic oxides of metals which do not form water-insoluble hydroxides provided said metals can be precipitated from aqueous solutions as salts such as the carbonates or nitrates which are converted to the corresponding oxides during the subsequent heating and/or sintering process.

Accordingly, there is contemplated within the ambit of the present invention a process for producing a polycrystalline barium titanate ceramic which comprises reacting equimolar amounts of barium ion and titanium (IV) with carbonate ion and hydroxide ion in aqueous medium to produce a gelatinous precipitate consisting of barium carbonate and hydrous titanium dioxide; separating the gelatinous precipitate from solution; heating the gelatinous precipitate at a temperature and for a time sufficient to convert the gelatinous precipitate to barium titanate and heating said barium titanate at a temperature and for a time sufficient to effect the sintering and substantially maximum densification thereof.

Barium titanate is useful in the manufacture of piezoelectric transducers and capacitors.

As sources of barium, titanium (IV) and carbonate ions there can be used barium chloride, barium nitrate, barium acetate, titanium tetrachloride, titanium tetrabromide, ammonium carbonate and the like. The process steps, i.e. precipitation, isolation, heating and sintering are carried out substantially as described above.

The ceramic oxides as provided by the instant process can be adapted to a specific end use or converted to a final product by conventional methods of fabrication such as molding or machining.

It will be understood that small amounts of additional ingredients well known in the ceramics art such as pigments, binders, sintering aids and the like which facilitate fabrication of the ultimate product can be incorporated in the ceramic oxides without departing from the spirit of the invention. Thus, the incorporation of small amounts of additional metals, e.g. lithium, aluminum, indium, magnesium, copper, manganese, bismuth, tin and the like, in the ferrites to improve their electrical properties is well known and is considered within the purview of the present invention.

The above-noted ceramic oxides have well recognized applications in industry, science and technology and when produced in accordance with the process of this invention are obtained efficiently and economically and are endowed with good to excellent physical properties. Thus the ceramic oxides are substantially nonporous with densities very near the theoretical density. Representative examples had densities in the range of 95.5-99.4% of theory. Magnetic properties of a few representative crude ferrite ceramics indicated applicability of the latter in the field of electronics.

In a composition aspect, the invention sought to be patented resides in a dental restorative composition comprising a blend of any of the novel ceramic materials of this invention and a polymerizable or polymerized bonding material which is compatible with the conditions of the oral cavity. The dental restorative composition of this invention comprises from about 10–90 percent, preferably 60 to 80 percent, by weight of finely divided ceramic, the remainder of said composition, from about 10–90 percent by weight, comprising a dentally acceptable polymerizable or polymerized bonding material together with known appropriate polymerization catalysts such as aliphatic ketone peroxides, benzoyl peroxide, etc., reactive diluents such as di-, tri- and tetra- ethylene glycol dimethacrylate, hardeners such as N-3-oxohydrocarbon-substituted acrylamides as described in U.S. Pat. No. 3,277,056, issued Oct. 4, 1966, promoters or accelerators such as metal acetyl acetonates, tertiary amines, e.g. N,N-bis-(2-hydroxyethyl)-p-toluidine, etc., or cross linking agents such as zinc oxide, etc., which are present in an amount ranging from about 0.01 to 45 percent by weight of the total composition. Although not essential, a surface-active comonomer or keying agent such as the reaction product of N-phenyl glycine and glycidyl methacrylate as described in U.S. Pat. No. 3,200,142, issued Aug. 10, 1965, methacryloxypropyltrimethoxysilane, 3,4-epoxycyclohexylethyltrimethoxysilane, vinyltrichlorosilane, etc., may be added to said composition in an amount ranging from 0.05 to 10 percent by weight of the total composition. The bonding or keying agent promotes bonding of the ceramic material to the resin and of the dental filling composition to the natural tooth. Thus, the ceramic products provided by this invention are comminuted to a suitable particle size of from about 5 to 100 microns using conventional milling techniques and then blended with an appropriate amount of a standard resin known in the dental restorative art such as hydroxyethyl methacrylate, polymethyl methacrylate, polyacrylic acid, propylene glycol fumarate phthalate unsaturated polyesters such as sold by Allied Chemical Co. as .23 LS8275 and by Pittsburgh Plate Glass as Selectron 580001, styrene modified unsaturated polyesters such as Glidden Glidpol 1008, G-136 and 4CS50, epoxy resins such as Ciba Araldite 6020, Union Carbide ERL2774 and the bisacrylate monomer prepared from glycidyl methacrylate and bisphenol A shown in U.S. Pat. No. 3,066,112, issued Nov. 27, 1962. The resin may comprise a single monomer or a mixture of two or more comonomers. Additives such as dyes, inorganic pigments and fluorescent agents may be optionally added to the above composition according to the principles known in the art concerning these materials. It is convenient to blend the resin, ceramic and optional ingredients such as silane bonding agents, dyes, inorganic pigments or fluorescent agents prior to the addition of the catalyst, hardener, cross-linking agent, promoter or accelerator. However, the order in which the ingredients are mixed is not critical and said ingredients may be blended simultaneously. Utilizing conventional techniques the composition thus produced can be used as a dental filling material, a dental cement, a cavity liner, a pulp capping agent or the composition can be cast in a suitable mold to produce an artificial tooth or set of teeth.

It is of course highly advantageous that material used in the oral cavity be caries resistant. This object is readily achieved in the practice of the present invention by adding from about 0.01 to 1 percent fluoride ion such as ammonium or stannous fluoride to the suspension of freshly precipitated hydroxylapatite. The ceramic produced by sintering of the resulting product is highly resistant to attack by lactic, acetic or citric acid, a standard in vitro method of determining caries resistance. Alternatively, resistance to caries can be imparted to the finished ceramic by exposing the same to a 0.5 to 5 percent aqueous solution of sodium fluoride for about 12 hours to five days. Preferably, the ceramic body is allowed to stand in about 5 percent aqueous sodium fluoride for approximately 4 days.

It will of course be appreciated by those skilled in the ceramics art that in addition to organic and inorganic binders and fluoride ion the ceramic materials provided by the present invention may also contain small amounts of other elements which although not changing the essential nature of the ceramic products may impart useful characteristics thereto. For example, it is known that barium and strontium will incorporate into the apatite crystal lattice and that these elements are considerably more opaque to X-rays than calcium. Therefore the addition of a small amount of barium or strontium ion to the calcium ion prior to reaction of the latter with phosphate ion will ultimately result in a barium or strontium-doped hydroxylapatite ceramic which when used in a dental restorative composition as described hereinabove would provide sufficient X-ray absorption to allow detection of the filled tooth. Magnesium which will also incorporate into the apatite crystal lattice is known to retard the crystallization of hydroxylapatite while promoting the crystallization of whitlockite [Eanes et al., Calc. Tiss. Res. 2, 32 (1968)]. Thus the addition of a small amount of magnesium ion to the calcium ion prior to reaction of the latter with phosphate ion will favor the formation of whitlockite thereby ultimately affording a whitlockite-enriched biphasic ceramic.

Both novel and known ceramic materials obtained as described above were characterized on the basis of one or more of the following: elemental analysis, density, X-ray diffraction, transmission electron microscopy, polarized light microscopy and mechanical and magnetic properties.

The invention is illustrated by the following examples without, however, being limited thereto.

EXAMPLE 1

To a stirred mixture containing 130 ml. of 1.63 N calcium nitrate (0.212 mole) and 125 ml. of concentrated aqueous ammonia there was added dropwise over a period of approximately 20 minutes a mixture containing 16.75 g. (0.127 mole) of diammonium hydrogen phosphate, 400 ml. of distilled water and 150 ml. of concentrated ammonia. The resulting suspension was boiled 10 minutes, cooled in an ice-bath and filtered. The filter cake was pressed with a rubber dam and then dried overnight at 95° C. A sample of the resulting, hard, porous, brittle cake was heated in an electric kiln over a period of 115 minutes up to a final temperature of 1230° C. and then cooled to room temperature to give a strong, hard white translucent ceramic product.

Standard elemental analyses of the final ceramic product and also of the dried hydroxylapatite prior to sintering yielded the following results based on $Ca_{10}(PO_4)_6(OH)_2$:

|  | Calc'd. | Dried, Unsintered Hydroxylapatite | Ceramic |
| --- | --- | --- | --- |
| Ca | 39.89% | 37.4% | 39.6% |
| P | 18.5% | 17.5% | 18.9% |
| $H_2O$ | 0% | 1% | — |
| Ca/p | 1.667 | 1.65 | 1.62 |

Examination of a thin section of the ceramic by polarized light microscopy at 130× and 352× indicated the material to be essentially free of whitlockite. The absence of birefringence and discernible structural features such as crystallite shape, orientation, boundaries, etc. indicated a microcrystalline structure. A comparison with the optical micrographs of a thin section of the sintered compressed tablet reported by Monroe et al. (supra) showed the two materials to be structurally dissimilar.

X-ray diffraction measurements were carried out in conventional manner. The interplanar spacings were calculated and found to be virtually identical to the values given for hydroxylapatite by Donnay et al., Crystal Data, ACA Monogram No. 5,668 (1963). The X-ray data further indicated the absence of whitlockite in any amount greater than about 2 to 3 percent, the minimum concentration sensitivity of the diffractometer.

EXAMPLE 2

A solution containing 79.2 g. (0.60 mole) of diammonium hydrogen phosphate in 1500 ml. of distilled water was adjusted to pH 11–12 with approximately 750 ml. of concentrated ammonia. Additional distilled water was added to dissolve precipitated ammonium phosphate giving a total volume of 3200 ml. If necessary the pH was again adjusted to 11-12. This solution was added dropwise over 30–40 minutes to a vigorously stirred solution containing 1 mole of calcium nitrate in 900 ml. of distilled water previously adjusted to pH 12 with approximately 30 ml. of concentrated aqueous ammonia and then diluted to a volume of 1800 ml. with distilled water. When the addition was complete, the resultant gelatinous suspension was stirred an additional 10 minutes, and then boiled 10 minutes, removed from the heat, covered, and allowed to stand 15–20 hours at room temperature. The supernatant was decanted and the remaining suspension was centrifuged at 2000 rpm for 10 minutes. The resulting sludge was re-suspended in 800 ml. of distilled water and again centrifuged at 2000 rpm for 10 minutes. Sufficient distilled water was added to the residual solids to give a total volume of 900 ml. Vigorous shaking afforded a homogeneous suspension essentially free of large fragments or aggregates.

The entire suspension was poured into a büuchner funnel at one time and filtered with application of a weak vacuum. When the filter cake began to crank a rubber dam was applied and the vacuum increased. After one hour, the dam was removed and the crack-free, intact filter cake was transferred to a flat surface, and dried 15 hours at 90°–95° C. to give 90–100 g. of white, porous, brittle pieces of hydroxylapatite. Fragments of from one to four $cm^2$. and free of cracks and fissures were placed in an electric kiln and the temperature was raised to 1200° C. over a period of 100 min. after which time the kiln and its contents were allowed to cool to room temperature. There resulted pieces of hard, dense, non-porous, white, translucent ceramic material.

| Analysis: | Calc'd. | Dried, Unsintered Hydroxylapatite | Ceramic |
|---|---|---|---|
| Ca | 39.89% | 36.5, 36.8% | 31.7, 38.0% |
| P | 18.5% | 21.7% | 22.8, 19.0, 18.8 |
| Ca/p | 1.667 | 1.30; 1.31 | 1.08, 1.55, 1.56 |

Subsequent to carrying out the above analyses it was discovered that the analytical technique used did not allow complete dissolution of the samples and the results are therefore inaccurate and highly variable. X-ray diffraction data however indicated the composition to be 95% hydroxylapatite and 5% whitlockite.

Two-stage replica samples were made by shadowing a collodion replica of the sample surface with chromium and then coating it with carbon. Transmission electron microscopic examination of the replicated samples revealed a fairly uniform grain size with no evidence of pores or second phase precipitate in either grain boundaries or within the grains themselves in any amount greater than about 0.5%, the minimum concentration sensitivity of the electron microscope. A sample of the ceramic was then polished on SiC paper to 600 grit, then polished to 3 micrometer diamond paste on a metallographic wheel covered with fine nylon cloth. The sample was then etched with 4% hydrofluoric acid for 30 seconds. Replicas were then made of the polished and etched surface and then viewed by electron microscopy. Again no second phases were observed in the grain boundaries, however there was some evidence of small second phase particles in the grain bulk. It was subsequently learned that these second phase particles were probably due to the formation of calcium fluoride on the ceramic surface as a result of the hydrofluoric acid etching process. Subsequently obtained samples were etched with 0.15 M lactic acid, pH 2.4, for 10 minutes and electron microscopy thereof revealed none of the second phase particles observed when the same samples had been etched with hydrofluoric acid.

As previously mentioned, compression and tensile strength are known to vary with the shape, dimensions and surface characteristics of the material tested. Thus compression strength was determined for both unpolished and lightly polished samples and found to be 56,462 psi ±16,733 psi and 131,000 psi±18,400 psi respectively.

Tensile strength was determined on unpolished samples by the standard three point bending test and found to be 9,650 psi±3,320 psi.

The modules of elasticity was determined by standard procedures and found to be $6.3 \times 10^6$ psi.

The thermal expansion coefficient was found to be linear between 25° C. and 225° C. with a value of $11 \times 10^{-6}/°C. \pm 10\%$.

A hardness value of 480 was found using the standard Knoop method. The same value was obtained irrespective of the direction of the applied force indicating thereby that the material was isotropic.

Porosity was determined qualitatively by immersing the test material in a fuchsin dye for 15 minutes, washing the same with water, drying, and then examining the test material for traces of remaining dye. This test was performed simultaneously on the non-porous form of the ceramic provided by this invention, a sintered compressed tablet of hydroxylapatite, and a natural tooth. The sintered compressed tablet showed considerable retention of the dye whereas the novel ceramic of the present invention and the natural tooth exhibited no visible retention of dye. In another method, the test material was immersed in 6 N aqueous ammonia for 15 minutes, then washed with water, dried and wrapped in moist litmus paper. Any ammonia remaining entrapped in surface pores causes the surrounding litmus paper to turn blue. When this test was performed simultaneously on the ceramic of this invention, a sintered compressed tablet of hydroxylapatite, and a natural tooth, the litmus paper in contact with the sintered compressed tablet turned blue thereby indicating the presence of entrapped ammonia in the tablet. No color change was observed in the litmus paper contacting either the novel ceramic of the present invention or the natural tooth.

In subsequently prepared samples porosity was determined quantitatively from electron micrographs using the method described by Hilliard and Cahn [Trans. Met. Soc. AIME 221, 344 (1961)].

EXAMPLE 3

Following a procedure similar to that described in Example 2 but starting with 3 moles of calcium nitrate and 1.8 moles of diammonium hydrogen phosphate there was obtained 304 g. of white, brittle, porous hydroxylapatite.

| Analysis: | Calc'd. | Found |
|---|---|---|
| Ca | 39.89 | 40.0 |
| P | 18.5 | 18.6 |
| Ca/p | 1.667 | 1.66 |

Sintering at 1100° C. for one hour produced a hard, white, translucent ceramic having a density of 3.10 $g/cm^3$. X-ray diffraction indicated the material was homogeneous hydroxylapatite. Electron microscopic examination revealed the absence of pores or second phase precipitates and a crystallite size distribution in the range 0.7 to 3 microns as determined by the linear slope method described by Hilliard (Metal Progress, p. 99, May 1964). The average tensile strength of an unpolished sample as determined by the standard three-point bend test was found to be 16,200 psi.

EXAMPLE 4

A. By following a procedure similar to that described in Example 2 but employing one-half the quantities used therein, an estimated 50 g. of hydroxylapatite was precipitated from aqueous solution. Following centrifugation and decantation the residual mineral sludge was resuspended in sufficient water to give a total volume of 1 liter and homogenized in a Waring blender for 2 minutes.

B. A mixture containing 0.5 g. of powdered cellulose (<0.5μ) in 200 ml. of water was blended in a Waring blender for 3 minutes. A 100 ml. aliquot of the homogeneous aqueous suspension of hydroxylapatite was then added and the resulting mixture blended another 5 minutes. The suspension was then filtered, and the filter cake dried and sintered according to Example 2. The filter cake after drying showed very little cracking and the ceramic product produced by sintering was slightly porous as indicated by the fuchsin dye test described hereinabove.

C. A mixture containing 0.5 g. of shredded surgical cotton in 200 ml. of water was blended in a Waring blender for 45 minutes or until a nearly homogeneous suspension was obtained. A 100 ml. aliquot of the homogeneous aqueous suspension of hydroxylapatite described in Example 4A was then added and blending continued an additional 15 minutes. The resulting suspension was filtered and the filter cake dried and sintered according to Example 2. The ceramic product remained intact and was visibly porous.

EXAMPLE 5

A. A mixture containing 5 g. of collagen (bovine Achilles tendon) in 300 ml. of water was blended in a Waring blender for 5 minutes. The collagen occluded large amounts of water to form a thick gelatinous mass. A small amount of finely divided collagen (20-30 mg.) remained in suspension.

B. The suspension of the finely divided collagen (250 ml.) was decanted and blended in a Waring blender for 5 minutes with a 100 ml. aliquot of the homogeneous aqueous suspension of hydroxylapatite described in Example 4A. The resulting mixture was filtered and the filter cake dried and sintered according to Example 2. The ceramic product remained intact and appeared substantially non-porous.

C. Approximately 20 percent of the thick gelatinous collagen was blended in a Waring blender for 6 minutes with 150 ml. of the homogeneous aqueous suspension of hydroxylapatite described in Example 4A. The resulting mixture was filtered and the filter cake dried and sintered according to Example 2. The dried cake prior to sintering remained intact and had considerable mechanical strength. The ceramic produced by sintering was hard, strong and visibly porous.

EXAMPLE 6

Samples of the ceramic product prepared according to Example 2 were allowed to stand in 1 percent aqueous sodium fluoride for 12 hours. These materials together with samples of untreated ceramic and natural teeth were then exposed to 10 percent lactic acid. After 3 days the fluoride-treated ceramic showed substantially less attack by lactic acid than either the untreated ceramic or the natural tooth enamel. When allowed to stand in 1 percent aqueous sodium fluoride for 3 days the ceramic was not visibly attacked by lactic acid after 3 days, and after 1 month had undergone only slight decomposition whereas untreated samples were heavily decomposed.

EXAMPLE 7

By following a procedure similar to that described in Example 2 but employing one-half the quantities used therein, an estimated 50 g. of hydroxylapatite was precipitated from aqueous solution. Following centrifugation the mineral sludge was suspended in sufficient water to give a total volume of 500 ml. The suspension was divided into ten equal portions each of which was diluted with 50 ml. of water and treated with ammonium fluoride as follows: To samples 1, 2, 3, 4 and 5 there was added respectively 0, 0.1, 0.5, 1.0 and 2.0 ml. of aqueous ammonium fluoride containing 0.00085 g. $F^\ominus$/ml. Samples 6, 7 and 8 were treated with 0.5, 1.0 and 10.0 ml. respectively of aqueous ammonium fluoride containing 0.0085 g. $F^\ominus$/ml. To samples 9 and 10 were added 2.0 and 4.0 ml. respectively of aqueous ammonium fluoride containing 0.045 g. $F^\ominus$/ml. The suspensions were then shaken on a rotary shaker for 1.5 hours and filtered. The filter cakes were pressed 15 minutes with a rubber dam, dried 2 days at 95° C. and then heated in an electric kiln to a temperature of 1200° C. The resulting ceramics were ground into fine powders and sieved through a No. 325 mesh screen. Eighty milligrams of each of the powder samples was mixed with 80 ml. of pH 4.1 sodium lactate buffer solution (0.4 M) at 23° C. and shaken on a Burrell wrist-action shaker. At times of 2, 9, 25 and 40 minutes after mixing, a 3-ml. aliquot was removed from each sample mixture, immediately filtered to remove undissolved sample and the amount of solubilized ceramic determined by a colorimetric assay procedure. The results are given in Table A. For purposes of comparison a sintered portion of sample 1 was allowed to stand 4 days in 1 ml. of 5% sodium fluoride. The solid was separated, washed thoroughly with water, dried and then subjected to the above-described dissolution assay as Sample 1A. The results are included in Table A. It will, of course, be appreciated that the above-described experimental conditions do not approximate in vivo conditions but were chosen so as to permit sufficient solubilization of sample within a reasonable length of timing affording thereby an accurate assessment of the relative effect of fluoride ion concentration. Thus, in vivo dissolution rates for ceramic hydroxylapatite are expected to be considerably less than the above-observed rates in the strong lactate buffer.

TABLE A

Relative Dissolution Rates of Fluoridated Ceramic Hydroxylapatite

| Sample No. | Fluoride Content (PPM) | | % Dissolved | | | |
|---|---|---|---|---|---|---|
| | Added | Found | 2 min. | 9 min. | 25 min. | 40 min. |
| 1 | 0 | — | 9.2 | 18.5 | 32.0 | 39.7 |
| 2 | 17 | 19 | 9.2 | 18.8 | 29.3 | 39.0 |
| 3 | 85 | 190[a] | 8.9 | 17.6 | 30.0 | 38.3 |
| 4 | 170 | 190 | 10.3 | 18.3 | 30.5 | 37.5 |
| 5 | 340 | 216 | 9.9 | 18.1 | 29.7 | 35.2 |
| 6 | 850 | 226 | 8.8 | 17.1 | 27.7 | 33.0 |
| 7 | 1,700 | 470 | 7.9 | 18.1 | 25.7 | 29.8 |
| 8 | 17,000 | 1,460 | 6.7 | 12.1 | 19.7 | 23.3 |
| 9 | 18,000 | 1,700 | 6.3 | 11.5 | 19.7 | 23.3 |
| 10 | 36,000 | 2,307 | 5.9 | 11.3 | 17.6 | 21.0 |
| 1A | — | — | 3.7 | 7.1 | 13.7 | 18.7 |

[a]An apparently incorrect assay.

EXAMPLE 8

Large fragments of dried filter cake about 3-4 mm. thick prepared according to Example 2 and having Ca/P=1.64-1.66 were scored and broken into rectangular plates about 14-15 mm. long and 7-8 mm. wide and a small hole was bored through one end. One thousand of these plates were then sintered according to Example 2, and polished to a high gloss using standard lapidary techniques. The resulting ceramic bodies having a density of 3.12–3.14 g/cm$^3$, an average compression strength of about 121,000 psi and an average tensile strength of about 14,200 psi were in the form of rectangular plates approximately 10–11 mm. long, 4–5 mm. wide and 2–3 mm. thick and having a hole at one end through which a length of wire was attached. The plates, which could thereby be suspended to any desired depth in a test tube, were used as test surfaces in the evaluation of dental plaque inhibiting agents as described hereinabove.

EXAMPLE 9

A solution containing 0.24 mole of diammonium hydrogen phosphate in 600 ml. of distilled water was adjusted to pH 11.4 with 340 ml. of concentrated ammonia and the final volume brought to 1280 ml. with distilled water. This solution was added dropwise over 30 minutes to a vigorously stirred solution containing 0.4 mole of calcium nitrate in 360 ml. of distilled water previously adjusted to pH 11 with concentrated aqueous ammonia and diluted to a volume of 720 ml. with distilled water. The resulting suspension was stirred without boiling and 250 ml. aliquots were periodically removed and the products isolated, washed and dried as described in Example 2. All samples were then heated one hour at 1100° C. and the composition of the resultant ceramic products determined by X-ray diffraction. The results are given in Table B.

TABLE B

| Sample No. | Stirring Time | Standing Time Before Isolation | Elemental Analysis | | | Phases observed by X-Ray Diffraction | |
|---|---|---|---|---|---|---|---|
| | | | % Ca | % P | Ca/P | % Hydroxylapatite | % Whitlockite |
| 1 | 5 min. | — | 36.6 | 18.2 | 1.55 | 23 | 77 |
| 2 | 45 min. | — | — | — | — | 21 | 79 |
| 3 | 2 hr. | — | 36.6 | 18.0 | 1.57 | 39 | 61 |
| 4 | 4.5 hr. | — | — | — | — | 98 | 2$^a$ |
| 5 | 7 hr. | — | 37.0 | 17.0 | 1.68 | 98 | 2$^a$ |
| 6 | 7 hr. | 17 hr. | 37.2 | 17.0 | 1.69 | 100 | 0 |
| 7 | 24 hr. | — | 37.4 | 17.1 | 1.69 | 100 | 0 |
| 8 | 48 hr. | — | 37.4 | 16.8 | 1.72 | 100 | 0 |

$^a$These values border on the minimum concentration sensitivity of the X-ray diffractometer (2%–3%) and the accuracy thereof is thus questionable. Samples 4 and 5 were also found to be slightly porous (Volume fraction of pores = 0.0186 and 0.0161 respectively).

EXAMPLE 10

A. Following a procedure similar to that described in Example 2 but using 0.3 moles of calcium nitrate and 0.2 moles of diammonium hydrogen phosphate there was obtained a hard, brittle, porous product having the following elemental composition: Ca=38.85%; P=19.77%; Ca/P=1.52. This material was heated 1 hour at 1200° C. to give a strong, hard, white, somewhat opaque ceramic material comprising approximately 40% hydroxylapatite and 60% whitlockite as indicated by X-ray diffraction.

B. When the above reaction was carried out with inverse addition of the starting materials there obtained a product comprising approximately 40% hydroxylapatite and 60% whitlockite, and having Ca/P=1.52 and a density of 2.982 g/cm$^3$.

EXAMPLE 11

A solution containing 0.0625 mole of diammonium hydrogen phosphate in 150 ml. of distilled water was treated with 95 ml. of concentrated ammonia and the final volume brought to 320 ml. with distilled water. This solution was added dropwise over 30 minutes to a vigorously stirred solution containing 0.1 mole of calcium nitrate and 2.5 ml. of concentrated ammonia in 180 ml. of distilled water. The resulting suspension was stirred 5 minutes then cooled in ice for 45 minutes and the suspended solid isolated, washed and dried as described in Example 2 to give a hard, brittle, porous, white solid having the following elemental compositions: Ca=35.4%; P=18.59%; Ca/P=1.46. This material was heated 1 hour at 1350° C. to give a strong, hard, somewhat opaque ceramic product comprising approximately 14% hydroxylapatite and 86% whitlockite as indicated by X-ray diffraction.

EXAMPLE 11A

A solution containing 2 moles of diammonium hydrogen phosphate in 4.5 l. of distilled water was brought to pH 11–11.5 by addition of 2.2 l. of concentrated aqueous ammonia. Additional distilled water was added to dissolve the precipitated ammonium phosphate to give a total volume of 9.6 l. The pH was again adjusted to 11–11.5 with 800 ml. of concentrated aqueous ammonia. This solution was added dropwise over 45 minutes to a vigorously stirred solution containing 3 moles of calcium nitrate in 5.4 l. of distilled water adjusted to pH 11–11.5 with 90 ml. of concentrated aqueous ammonia. The resulting suspension was stirred 21 hours at room temperature and the product was isolated, washed and dried as previously described. A sample was sintered 1 hr. at 1100° C. to give a strong, hard, nonporous ceramic having a calcium to phosphorus ratio of 1.53 and comprising 20% hydroxylapatite and 80% whitlockite as indicated by X-ray diffraction.

EXAMPLE 11B

Following a procedure similar to that described in Example 2 but employing 3 moles of calcium nitrate and 1.8 moles of diammonium hydrogen phosphate there was obtained an aqueous suspension of hydroxylapatite having a total volume of 15 l. Following removal of 2.3 l. of the suspension for assay purposes the remaining 12.7 l. was stirred while the pH was adjusted to 11.5 with 4.4 l. of concentrated aqueous ammonia, and the resulting mixture was treated dropwise over 0.5 hour with a solution containing 76.2 ml. of 1.01 M aqueous calcium nitrate diluted to 450 ml. with distilled water and adjusted to pH 11.5 with 5 ml. of concentrated aqueous ammonia. After addition was complete stirring was continued an additional 10 minutes. After standing overnight the product was isolated, washed and dried as previously described and then sintered at 1100° C. for one hour to afford a strong, translucent ceramic having a surface pH of 10.8, a calcium to phosphorus ratio of 1.66 and which X-ray diffraction indicated to be substantially pure hydroxylapatite.

The products of Examples 1–11 correspond to the articles of manufacture of this invention and have the physical characteristics thereof as described hereinabove.

The articles of manufacture produced according to Examples 4 and 5C although comprising the same material produced according to Examples 1 and 3 have introduced therein spaces or pores of varying number and size. It will be obvious, of course, that the introduction of pores into said articles effects a change in the physical properties thereof, for example, a reduction in compression strength, tensile strength, elasticity and hardness.

EXAMPLE 12

A composition suitable as a dental cement and dental filling agent was prepared as follows:

A. To a solution containing 20 mg. of the condensation product of N-phenylglycine and glycidyl methacrylate (described in U.S. Pat. No. 3,200,142 and referred to therein as NPG-GMA) in 7 ml. of ethanol there was added 2.0 g. of powdered ceramic hydroxylapatite. After swirling 5 minutes the ethanol was evaporated under vacuum at room temperature and the residual solid was dried 2 hrs. at 1 mm. Hg.

B. An 80-mg. sample of the above material was mixed with 0.4 mg. of benzoyl peroxide and 30 mg. of a 1:2 mixtur of hydroxyethyl methacrylate and the reaction product of bisphenol A and glycidyl methacrylate as described in U.S. Pat. No. 3,066,112 and referred to in the art as BisGMA. The resulting mixture was placed in a cylindrical steel mold wherein it hardened in 3–5 minutes. Compression strength was determined for four cyclindrical plugs so-prepared. The average value was 24,350 psi.

EXAMPLE 13

A mixture comprising 60 parts of powdered ceramic hydroxylapatite, 13 parts of hydroxyethyl methacrylate, 27 parts of the condensation product of bisphenol A and glycidyl methacrylate, 0.3 parts of N,N-bis-(2-hydroxyethyl)-p-toluidine and 0.8 parts of benzoyl peroxide was blended thoroughly to give a thin, free-flowing formulation useful as a dental pit and fissure sealant. The mixture was poured into a cylindrical steel mold wherein it hardened in about 3 minutes. Compression strength was determined for seven cyclindrical plugs so-prepared. The average value was 20,400 psi.

EXAMPLE 34

The following is an example of a formulation useful as a dental filling material.

To 5 ml. of 2-propanol was added 0.5 g. of powdered ceramic hydroxylapatite. The 2-propanol was then evaporated under vacuum at room temperature in order to remove any water of hydration from the surface of the ceramic. To 120 mg. of powdered hydroxylapatite so-treated was added 0.3 mg. of benzoyl peroxide followed by 40 mg. of a mixture comprising the condensation product of bisphenol A and glycidyl methacrylate, triethylene glycol dimethacrylate and N,N-bis-(2-hydroxyethyl)-p-toluidine which mixture is sold by Lee Pharmaceuticals under the tradename Epoxylite ® HL-72. The mixture was spatulated to a smooth paste and placed into cylindrical steel molds and allowed to stand 4 hours. The cylindrical plugs were removed from the molds and 3 specimens were tested and found to have an average compression strength of 22,300 psi.

EXAMPLE 15

To a solution containing 30 mg. of the condensation product of N-phenylglycine and glycidyl methacrylate in 7 ml. of ethanol was added with swirling 1 g. of powdered ceramic hydroxylapatite. The ethanol was evaporated under vacuum at room temperature. To a mixture containing 180 mg. of powdered ceramic hydroxylapatite so-treated and 3.0 mg. of benzoyl peroxide was added to 74 mg. of a mixture containing 60 parts of the condensation product of bisphenol A and glycidyl methacrylate and 40 parts of triethylene glycol dimethacrylate and the resulting aggregate spatulated to a smooth paste which was placed into cylindrical steel molds and allowed to stand 3 hours. The cylindrical plugs were removed from the molds and 4 specimens were tested and found to have an average compression strength of 22,300 psi.

EXAMPLE 16

A composition suitable as a dental and orthodontic cement or as a temporary dental filling agent was prepared by mixing together 100 mg. of powdered ceramic hydroxylapatite, 300 mg. of zinc oxide and 300 mg. of 40% aqueous polyacrylic acid. The resulting mixture was placed in cylindrical steel molds wherein it hardened in about 3–5 minutes. The cylindrical plugs were removed from the molds and 4 specimens were tested and found to have an average compression strength of 12,400 psi. Another 5 specimens were found to have an average diametral tensile strength of 1630 psi. The 40% aqueous polyacrylic acid and the zinc oxide were obtained as the liquid and solid components respectively of a commercial polycarboxylate cement available from ESPE G.m.b.H., West Germany, under the trade name Durelon®.

EXAMPLE 17

A composition suitable as a dental cement and dental filling agent was prepared by mixing together 6 parts by weight of 40 percent aqueous polyacrylic acid with a mixture containing 6 parts by weight of powdered ceramic hydroxylapatite and 4 parts by weight of zinc oxide. The resulting composition had a setting time of about 5 to 10 minutes. The 40 percent aqueous polyacrylic acid and the zinc oxide were obtained as the liquid and solid components respectively of a commercial polycarboxylate cement available from ESPE G.m.b.H., West Germany, under the trade name Durelon®.

EXAMPLE 18

The following is an example of a dental filling composition:

| Ingredient | Percent by Weight |
| --- | --- |
| Styrene modified polyester resin (Glidden Glidpol G-136) | 29.2 |
| Benzoyl peroxide | 0.7 |
| Styrene | 0.6 |
| Methacryloxypropyltrimethoxysilane | 1.5 |
| Ceramic hydroxylapatite | 68.0 |

EXAMPLE 19

The following is an example of a composition suitable as a dental cement, cavity liner and pulp capping agent:

| Ingredient | Percent by Weight |
| --- | --- |
| Epoxy resin (Union Carbide ERL2774) | 67 |
| N-3-oxo-1,1-dimethylbutyl acrylamide | 23 |

| Ingredient | Percent by Weight |
|---|---|
| Ceramic hydroxylapatite | 10 |

EXAMPLE 20

The following is an example of a composition suitable for the fabrication of an artificial tooth or set of teeth.

A mixture containing 60 parts by weight of ceramic hydroxylapatite of approximately 150 to 200 mesh and 40 parts by weight of powdered polymethyl methacrylate is blended with approximately 15 parts by weight of liquid monomeric methyl methacrylate and the resulting mixture allowed to stand in a sealed vessel at room temperature until the material no longer adheres to the walls of the vessel and has a non-sticky plastic consistency. The material is then packed into an appropriate mold and the mold and its contents immersed in water which is heated to boiling over a period of about one hour and maintained at that temperature for 30 minutes. The mold is then allowed to air cool for about 15 minutes and finally cooled in cold tap water.

The biocompatibility of the novel ceramic form of hydroxylapatite afforded by the present invention was confirmed by implantation studies wherein it was found that no inflammatory response was elicited when chips of the ceramic prepared according to the method of Example 1 were implanted intraperitoneally in live rats or when inserted subcutaneously on the backs of live rabbits. After 28 days the animals were sacrificed and no resorption of the ceramic was evident.

Pellets of ceramic hydroxylapatite prepared by a method similar to that described in Example 3 and having a density of about 3.11 g/cm$^3$ and an average compression strength of about 147,800 psi were implanted in surgically created voids in the femurs of live dogs. The implants were monitored in vivo by periodic X-ray. After respective periods of one month and six months the animals were sacrificed and the femurs containing the implants were removed. The femurs were sectioned at the implant site and examined by both optical and scanning electron microscopy. Both the onemonth and six-months implants were characterized by normal healing, strong binding of new bone to the implant surface with no intervening fibrous tissue, no evidence of inflammation or foreign body response and no resorption of the implant material.

Example 21

To a stirred mixture containing 5 g. of magnesium hydroxide in 100 ml. of water was added dropwise sufficient nitric acid to produce a clear solution. The solution was filtered and added dropwise over 10 minutes to 100 ml. of stirred 20% aqueous ammonia. After addition was complete stirring was continued another 10 minutes. The resulting gelatinous precipitate was collected by filtration and heated 3 days at 95° C. The hard cake so obtained was slowly heated to 1600° C. and maintained at that temperature for 50 hours to give a translucent polycrystalline magnesium oxide ceramic having a density of 3.50 g/cm$^3$. The x-ray diffraction pattern of the product was virtually identical to the ASTM standard for cubic magnesium oxide. Scanning electron microscopy revealed grain sizes ranging from 10 to 50 $\mu$m and some fine pores about 0.5 $\mu$m in diameter.

EXAMPLE 22

By following a procedure similar to that described in Example 21 but employing a water soluble aluminum salt there was obtained a polycrystalline aluminum oxide ceramic.

EXAMPLE 23

A solution containing 30 g. of ferric ammonium sulfate dodecahydrate in 200 ml. of distilled water was added dropwise over 10 minutes to 100 ml. of stirred 20% aqueous ammonia. After addition was complete stirring was continued another 10 minutes. The resulting gelatinous precipitate was collected by filtration and air-dried. The dried cake was placed in an electric kiln and the temperature was raised to 1200° C. over a period of 2 hours after which time the kiln and its contents were allowed to cool to room temperature. There resulted a polycrystalline$\alpha$-ferric oxide ceramic having a density of 5.21 g/cm$^3$. The X-ray diffraction pattern of the product was virtually identical to the ASTM standard for rhombohedral$\alpha$-Fe$_2$O$_3$. Scanning electron microscopy revealed grain sizes between 4 and 10 $\mu$m and a few fine pores about 0.4 $\mu$m in diameter.

EXAMPLE 24

A solution containing 29.1 g. (0.1 mole) of nickel nitrate hexahydrate in 500 ml. of distilled water and a solution containing 80.8 g. (0.2 mole) of ferric nitrate nonahydrate in 750 ml. of distilled water were combined and added in a rapid drip to 300 ml. of vigorously stirred 3 N aqueous sodium hydroxide. After the addition was complete stirring was continued an additional 20 minutes. The mixture was centrifuged 10 minutes at 2000 rpm. and the supernatant decanted. The residue was resuspended in 400 ml. of distilled water and again centrifuged 10 minutes at 2000 rpm. The supernatant was decanted and the process was repeated. The final residue was suspended in 500 ml. of water and the product collected by filtration. The resulting filter cake was heated 12 hours at 80° C.; 1 hour at 350° C.; from 350° C. to 500° C. at a rate of 100° C./hr. and then at a rate of 200° C./hr. up to a final sintering temperature of 1200° C. which was then maintained for 3 hours to give a polycrystalline nickel ferrite ceramic, NiFe$_2$O$_4$ having a density of 5.12 g./cm$^3$. The X-ray diffraction pattern was virtually identical to the ASTM standard for NiFe$_2$O$_4$ having a spinel structure. Electron microscopy revealed average grain sizes slightly larger than 1 $\mu$m and some pores at the grain boundaries. The product had a saturation magnetization of 221 Gauss/cm$^3$, a remnance of 45 Gauss/cm$^3$ and a permeability of 0.28.

When sintering was carried out at 1100° C. for 3 hours the resulting product had a density of 4.93 g./cm$^3$, a saturation magnetization of 227 Gauss/cm$^3$, a remnance of 167 Gauss/cm$^3$ and a permeability of 0.26. The grain size was slightly smaller and the pores were more numerous but smaller in diameter.

A sintering temperature of 1300° C. for 3 hours produced a product having a density of 5.13 g/cm$^3$, a saturation magnetization of 254 Gauss/cm$^3$, a remnance of 45 Gauss/cm$^3$ and a permeability of 0.27.

EXAMPLE 25

A solution containing 34.9 g. (0.12 mole) of cobalt nitrate hexahydrate in 400 ml. of distilled water was mixed with a solution containing 115.7 g. (0.24 mole) of ferric ammonium sulfate in 500 ml. of distilled water.

The combined solutions were cooled to 5° C. and added rapidly to 360 ml. of cold, vigorously stirred 3 N aqueous sodium hydroxide. The reaction mixture was worked up according to the procedure described in Example 23 to give a polycrystalline cobalt ferrite ceramic having a density of 4.99 g./cm$^3$. The X-ray diffraction pattern was virtually identical to the ASTM standard for CoFe$_2$O$_4$ having a spinel structure. Electron microscopy revealed grain sizes of 1 to 4 μm and a few pores at the grain boundaries. The product had a saturation magnetization of 398 Gauss/cm$^3$, a remnance of 527 Gauss/cm$^3$, an initial permeability of 0.20 and a maximum permeability of 0.31.

When sintering was carried out at 1100° C. for 3 hours the resulting ceramic was slightly more porous and had a density of 4.79 g./cm$^3$, a saturation magnetization of 410 Gauss/cm$^3$, a remnance of 877 Gauss/cm$^3$, an initial permeability of 0.11 and a maximum permeability of 0.29.

A sintering temperature of 1300° C. for 3 hours produced a product having a density of 5.16 g./cm$^3$, a saturation magnetization of 407 Gauss/cm$^3$, a remnance of 461 Gauss/cm$^3$, an initial permeability of 0.11 and a maximum permeability of 0.29.

EXAMPLE 26

A solution containing 22.0 g. (0.1 mole) of zinc acetate dihydrate in 250 ml. of distilled water and a solution containing 96.4 g. (0.2 mole) of ferric ammonium sulfate in 1 liter of distilled water were combined with stirring and brought to pH 7 by addition of concentrated aqueous ammonia. The resulting gelatinous suspension was stirred 1 hr. at room temperature and then centrifuged 10 minutes at 2000 rpm. The supernatant was decanted and the residue was resuspended in distilled water and again centrifuged 10 minutes at 2000 rpm. After decanting the supernatant the residue was suspended in water and the product collected by filtration. The filter cake was allowed to dry at room temperature and then heated 1 hour at 1100° C. to give a polycrystalline essentially non-porous zinc ferrite ceramic as indicated by X-ray diffraction and electron microscopy.

It is contemplated that by following a procedure similar to those described hereinabove but employing appropriate amounts of a water-soluble barium salt, a water-soluble titanium (IV) salt, ammonium carbonate and ammonium hydroxide, there will be produced a polycrystalline barium titanate ceramic.

I claim:

1. A process for producing a dense polycrystalline ceramic ferric oxide which comprises reacting ferric ion with hydroxide ion in aqueous medium to produce a gelatinous precipitate of the corresponding hydrous oxide; separating the gelatinous precipitate from solution; heating the gelatinous precipitate up to a temperature of at least 1000° C. but below that at which decomposition occurs and at a rate effective to produce a substantially fracture-free ceramic; and maintaining said temperature for sufficient time to effect the sintering and substantially maximum densification of the resulting product.

2. A process according to claim 1 for producing a dense polycrystalline ferric oxide ceramic which comprises reacting ferric ion with hydroxide ion in aqueous medium to produce a gelatinous precipitate of hydrous ferric oxide; separating said gelatinous precipitate from solution; heating the gelatinous precipitate up to a temperature of about 1100° C. at a rate effective to produce a substantially fracturefree ceramic; and maintaining said temperature for approximately one hour.

* * * * *